US00PP22330P2

(12) United States Plant Patent
Wood

(10) Patent No.: US PP22,330 P2
(45) Date of Patent: Dec. 13, 2011

(54) ***HYDRANGEA* PLANT NAMED 'JANE'**

(50) Latin Name: *Hydrangea paniculata*
Varietal Denomination: Jane

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 12/807,829

(22) Filed: Sep. 14, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Annette Para
(74) *Attorney, Agent, or Firm* — C. A. Whealy

(57) ABSTRACT

A new and distinct cultivar of *Hydrangea* plant named 'Jane', characterized by its compact, upright and mounded plant habit; freely branching habit; strong and sturdy stems that hold inflorescences upright; and large mophead-type inflorescences with numerous light green-colored sterile flowers that with development become greyed purple in color.

2 Drawing Sheets

Botanical designation: *Hydrangea paniculata.*
Cultivar denomination: 'JANE'.

BACKGROUND OF THE INVENTION

The present invention relates to a new and distinct cultivar of *Hydrangea* plant, botanically known as *Hydrangea paniculata* and hereinafter referred to by the name 'Jane'.

The new *Hydrangea* plant is a product of a planned breeding program conducted by the Inventor in Grand Haven, Mich. The objective of the breeding program was to develop new compact *Hydrangea* plants with strong stems and attractive leaf and flower coloration.

The new *Hydrangea* plant originated from an open-pollination in August, 2005 of the *Hydrangea paniculata* 'Limelight Variegated', not patented, as the female, or seed parent and an unknown selection of *Hydrangea paniculata* as the male, or pollen, parent. The new *Hydrangea* plant was discovered and selected by the Inventor in June, 2007 as a flowering plant within the progeny of the stated open-pollination in a controlled environment in Grand Haven, Mich.

Asexual reproduction of the new cultivar by softwood cuttings in a controlled environment in Grand Haven, Mich. since June, 2007 has shown that the unique features of this new *Hydrangea* plant are stable and reproduced true to type in successive generations of asexual reproduction.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Jane'. These characteristics in combination distinguish 'Jane' as a new and distinct cultivar of *Hydrangea* plant:

1. Compact, upright and mounded plant habit.
2. Freely branching habit.
3. Strong and sturdy stems that hold inflorescences upright.

4. Large mophead-type inflorescences with numerous light green-colored sterile flowers that with development become greyed purple in color.

Plants of the new *Hydrangea* differ from plants of the female parent, 'Limelight Variegated', in the following characteristics:

1. Plants of the new *Hydrangea* are more compact than plants of 'Limelight Variegated'.
2. Plants of the new *Hydrangea* have solid green-colored leaves whereas plants of 'Limelight Variegated' have variegated leaves.
3. Plants of the new *Hydrangea* have darker green-colored sterile flowers than plants of 'Limelight Variegated'; additionally, with development, sterile flowers of plants of 'Limelight Variegated' become white in color.

Plants of the new *Hydrangea* can be compared to plants of *Hydrangea paniculata* 'Limelight', disclosed in U.S. Plant Pat. No. 12,874. In side-by-side comparisons, plants of the new *Hydrangea* differ from plants of 'Limelight' in the following characteristics:

1. Plants of the new *Hydrangea* are more compact than plants of 'Limelight'.
2. Plants of the new *Hydrangea* have smaller leaves than plants of 'Limelight'.
3. Sterile flowers of plants of the new *Hydrangea* have thicker sepals than sterile flowers of plants of 'Limelight'.
4. With development, sterile flowers of plants of the new *Hydrangea* become greyed purple in color whereas sterile flowers of plants of 'Limelight' become white in color.

Plants of the new *Hydrangea* can also be compared to plants of *Hydrangea paniculata* 'Little Lamb', disclosed in U.S. Plant Pat. No. 15,395. In side-by-side comparisons, plants of the new *Hydrangea* differ from plants of 'Little Lamb' in the following characteristics:

1. Plants of the new *Hydrangea* have stronger stems and peduncles than plants of 'Little Lamb'.
2. Plants of the new *Hydrangea* and 'Little Lamb' differ in sterile flower color as plants of 'Little Lamb' have white-colored sterile flowers.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Jane' grown in a container.

The photograph on the second sheet is a close-up view of typical inflorescences of 'Jane' at various stages of development.

DETAILED BOTANICAL DESCRIPTION

Plants used for the aforementioned photographs and the following description were grown during the summer and autumn in an outdoor nursery in Grand Haven, Mich. and under conditions which closely approximate commercial *Hydrangea* production conditions. Plants of the new *Hydrangea* were three years old when the photographs and description were taken. In the following description, color references are made to The Royal Horticultural Society Colour Chart, 2001 Edition, except where general terms of ordinary dictionary significance are used.

Botanical description: *Hydrangea paniculata* 'Jane'.

Parentage:

*Female, or seed, parent.*—*Hydrangea paniculata* 'Limelight Variegated', not patented.

*Male, or pollen, parent.*—Unknown selection of *Hydrangea paniculata*, not patented.

Propagation:

*Type cutting.*—By softwood cuttings.

*Time to initiate roots, summer.*—About 20 days at temperatures of about 24° C.

*Time to produce a rooted young plant, summer.*—About three months at temperatures of about 24° C.

*Root description.*—Fine and thick; creamy white in color.

*Rooting habit.*—Freely branching; dense.

Plant description:

*Plant form and growth habit.*—Perennial deciduous shrub; compact, upright and mounded plant habit; broadly inverted triangle; strong and sturdy lateral branches; freely branching habit; vigorous growth habit.

*Plant height.*—About 50 cm.

*Plant diameter or area of spread.*—About 40 cm.

*Lateral branches.*—Length: About 20 cm. Diameter: About 3 mm to 4 mm. Internode length: About 2 cm to 3 cm. Texture: Smooth, glabrous. Strength: Strong, sturdy. Color, developing: Close to 60A. Color, developed: Close to 165A.

Foliage description:

*Arrangement.*—Opposite, simple.

*Length.*—About 6 cm.

*Width.*—About 3.5 cm.

*Shape.*—Ovate.

*Apex.*—Acute.

*Base.*—Obtuse.

*Margin.*—Serrulate.

*Texture, upper and lower surfaces.*—Pubescent; rugose.

*Venation pattern.*—Pinnate.

*Color.*—Developing leaves, upper surface: Close to 144A. Developing leaves, lower surface: Close to 144B. Fully expanded leaves, upper surface: Close to 141A; venation, close to 145A. Fully expanded leaves, lower surface: Close to 138A to 138B; venation, close to 145B.

*Petioles.*—Length: About 5 mm. Diameter: About 2 mm. Texture, upper and lower surfaces: Smooth, glabrous. Color, upper and lower surfaces: Close to 144A.

Flower description:

*Flower type and habit.*—Single sterile and fertile flowers arranged on large terminal and axillary mophead-type panicles; flowers face upright to outwardly.

*Fragrance.*—None detected.

*Natural flowering season.*—Continuous flowering throughout the summer, July until first frost, in Grand Haven, Mich.

*Flower longevity, fertile flowers.*—Flowers last about two weeks on the plant; flowers not persistent.

*Flower longevity, sterile flowers.*—Flowers last about four months on the plant; flowers persistent.

*Quantity of flowers.*—Freely flowering; about 42 fertile flowers and about 153 sterile flowers per inflorescence.

*Inflorescence height.*—About 12 cm.

*Inflorescence diameter.*—About 10 cm.

*Flower diameter, fertile flowers.*—About 3 mm.

*Flower depth (height), fertile flowers.*—About 3 mm.

*Flower diameter, sterile flowers.*—About 3 cm.

*Flower depth (height), sterile flowers.*—About 2 cm.

*Flower buds, fertile and sterile flowers.*—Length: About 5 mm. Diameter: About 4 mm. Shape: Ovoid. Color: Close to 145D.

*Petals, fertile flowers only.*—Arrangement: Five in a single whorl. Length: About 2 mm to 3 mm. Width: About 1 mm to 2 mm. Shape: Narrowly ovate. Apex: Acute. Base: Attenuate. Margin: Entire. Texture, upper and lower surfaces: Smooth, glabrous. Color: When opening, upper and lower surfaces: Close to 145D. Fully opened, upper and lower surfaces: Close to 145D; with development, color becoming closer to 155A.

*Sepals, fertile flowers.*—Quantity per flower: Five in a single whorl. Length: About 0.5 mm. Width: About 0.5 mm. Shape: Ovate. Apex: Acute. Base: Fused. Margin: Entire. Texture, upper and lower surfaces: Smooth, glabrous. Color, upper and lower surfaces: Close to 145B to 145C.

*Sepals, sterile flowers.*—Quantity per flower: About four in a single whorl. Length: About 1.8 cm. Width: About 1.3 cm. Shape: Elliptical to obovate. Apex: Obtuse. Base: Obtuse. Margin: Entire. Texture, upper and lower surfaces: Smooth, glabrous. Color: When opening, upper surface: Close to 144B. When opening, lower surface: Close to 144C. Fully opened, upper surface: Close to 145A; with development, color becomes closer to 186B. Fully opened, lower surface: Close to 145C.

*Peduncles, fertile and sterile flowers.*—Angle: Mostly upright. Strength: Strong, sturdy. Length: About 9 cm. Diameter: About 1 mm to 2 mm. Texture: Smooth, glabrous. Color: Close to 145B to 145C.

*Pedicels, fertile flowers.*—Angle: Erect to about 30° from vertical. Strength: Moderately strong. Length: About 1 mm. Diameter: About 1 mm. Texture: Smooth, glabrous. Color: Close to 145B to 145C.

*Pedicels, sterile flowers.*—Angle: Erect to about 30° from vertical. Strength: Strong. Length: About 1.4 cm. Diameter: About 1 mm. Texture: Smooth, glabrous. Color: Close to 145B to 145C.

*Reproductive organs, fertile flowers only.*—Stamens: Quantity per flower: About nine or ten. Anther shape: Rounded. Anther length: About 0.5 mm. Anther color: Close to 145D. Pollen amount: Scarce. Pollen color: Close to 145D. Pistils: Pistil quantity per flower: One. Pistil length: About 0.5 mm. Stigma shape: Two to three-lobed. Stigma color: Close to 146C. Style length: About 0.5 mm. Style color: Close to 146C. Ovary color: Close to 146C.

*Seeds.*—Quantity per inflorescence: Numerous. Size: Less than 0.1 mm by less than 0.1 mm. Color: Brown.

Disease/plant resistance: Plants of the new *Hydrangea* have been observed to be resistant to mildew. Plants of the new *Hydrangea* have not been observed to be resistant to pests or other pathogens common to *Hydrangea*.

Temperature tolerance: Plants of the new *Hydrangea* have been shown to be tolerant to temperatures ranging from about −30° C. to about 38° C.

It is claimed:

1. A new and distinct *Hydrangea* plant named 'Jane' as illustrated and described.

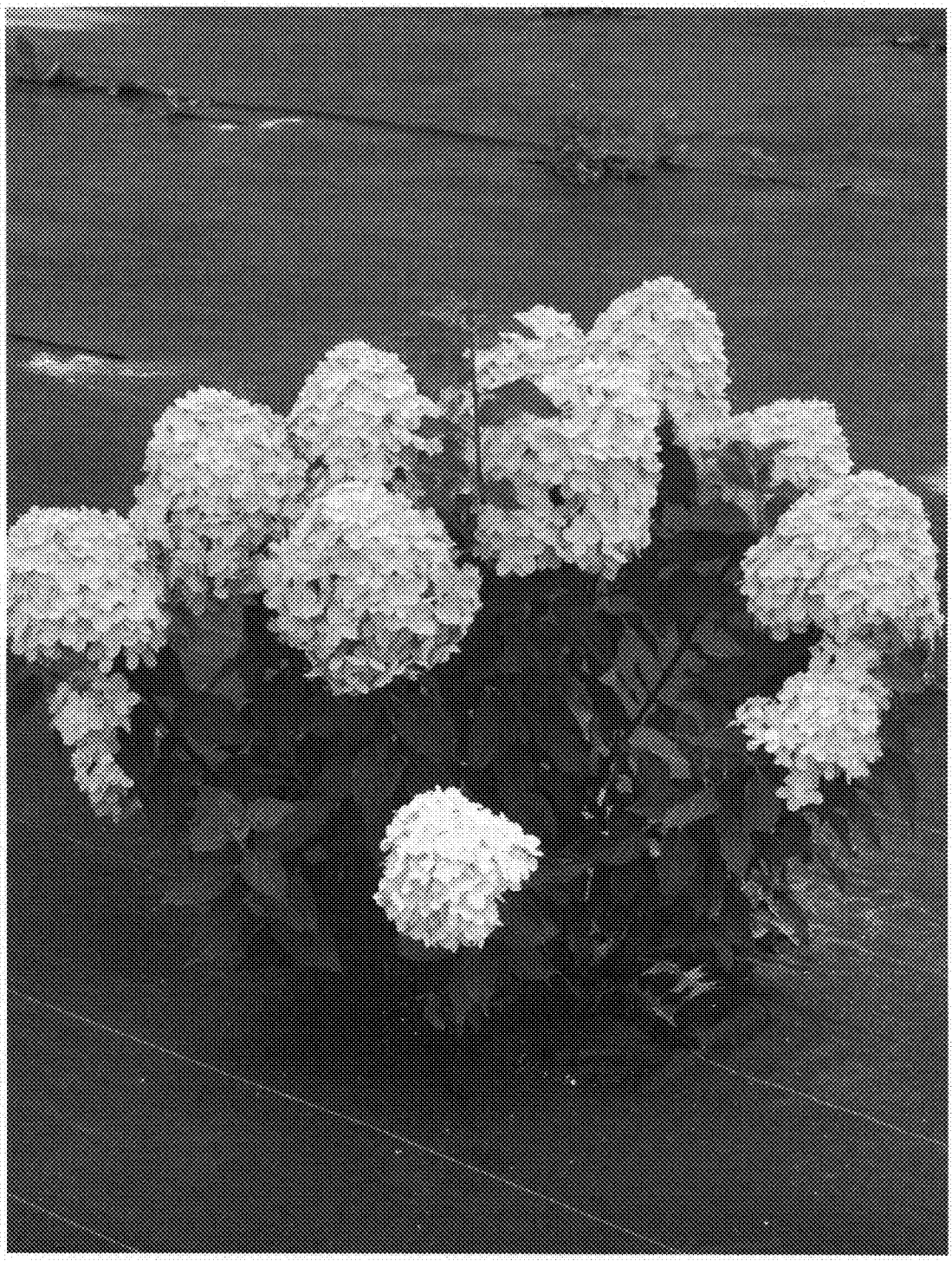

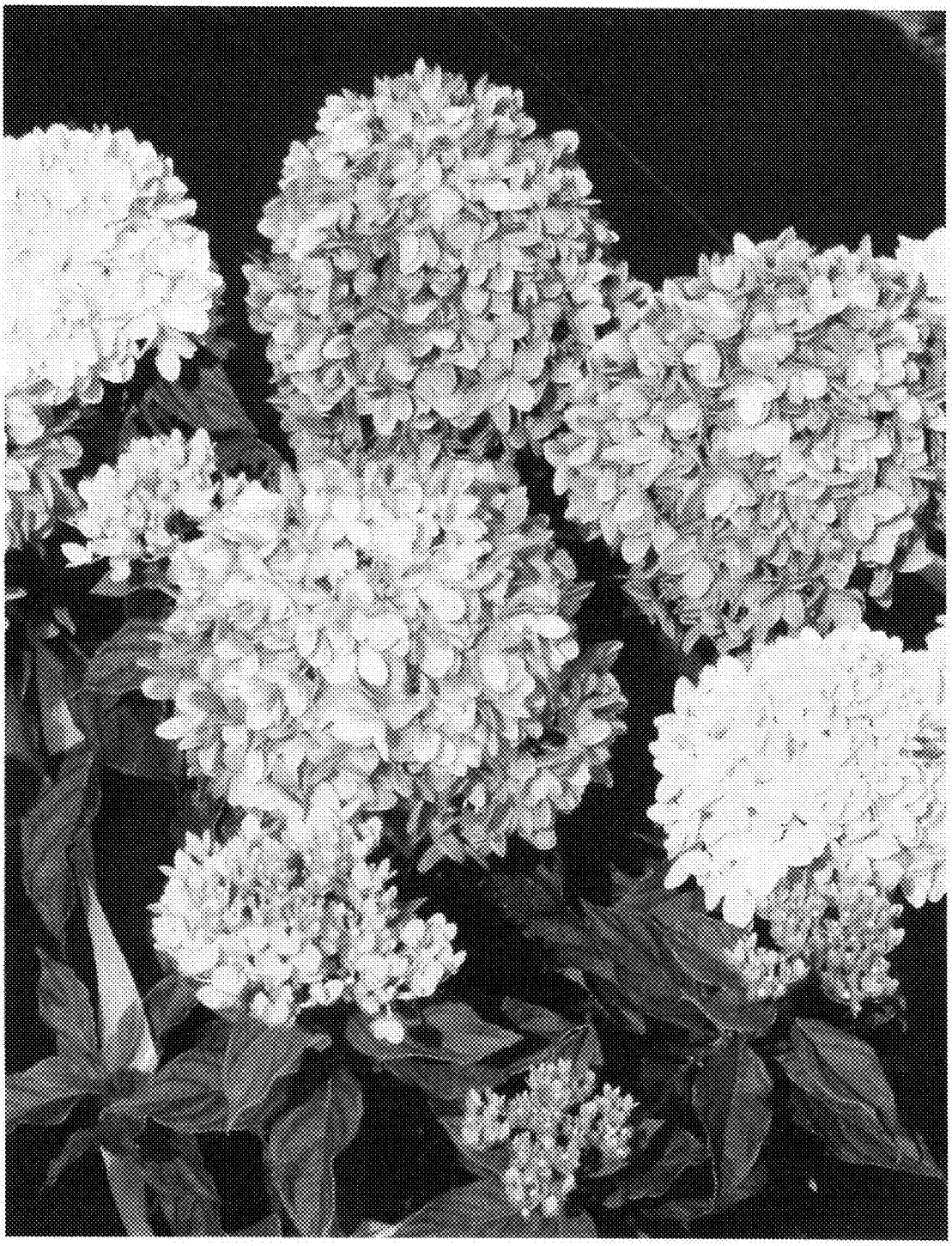

* * * * *